(12) United States Patent
Heidenfelder et al.

(10) Patent No.: US 7,011,772 B2
(45) Date of Patent: Mar. 14, 2006

(54) UV ABSORBING MIXTURE WITH TEXTILE FIBER AFFINITY

(75) Inventors: Thomas Heidenfelder, Roemerberg (DE); Gerhard Wagenblast, Wachenheim (DE); Jürgen Detering, Limburgerhof (DE); Thorsten Habeck, Meckenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 395 days.

(21) Appl. No.: 10/221,169

(22) PCT Filed: Mar. 27, 2001

(86) PCT No.: PCT/EP01/03470

§ 371 (c)(1),
(2), (4) Date: Sep. 18, 2002

(87) PCT Pub. No.: WO01/72935

PCT Pub. Date: Oct. 4, 2001

(65) Prior Publication Data

US 2003/0127633 A1    Jul. 10, 2003

(30) Foreign Application Priority Data

Mar. 28, 2000 (DE) .............................. 100 15 086

(51) Int. Cl.
*F21V 9/06* (2006.01)
*D06M 13/00* (2006.01)
*A61K 7/42* (2006.01)
*A61K 7/44* (2006.01)

(52) U.S. Cl. ..................... 252/589; 252/588; 8/115.51; 8/116.1; 424/59; 424/60; 424/402

(58) Field of Classification Search ............... 252/589; 8/116.1
See application file for complete search history.

(56) References Cited

U.S. PATENT DOCUMENTS

| 5,770,183 A | 6/1998 | Linares |
| 6,033,649 A | 3/2000 | Pittet et al. |

FOREIGN PATENT DOCUMENTS

| DE | 196 43 515 | 4/1998 |
| DE | 199 18 967 | 11/2000 |
| EP | 0 659 877 | 6/1995 |
| EP | 0 682 145 | 11/1995 |
| EP | 0 728 749 | 8/1996 |
| FR | 2 658 075 | 8/1991 |
| GB | 2 313 375 | 11/1997 |
| WO | 96/03486 | 2/1996 |
| WO | 97 44422 | 11/1997 |
| WO | 99 06014 | 2/1999 |

OTHER PUBLICATIONS

Earll, Mark, A Guide to Log P and pKa Measurements and Their Use, 1999, http://www.raell.demon.co.uk/chem/logp/logppka.htm, 1-23.*

* cited by examiner

*Primary Examiner*—Randy Gulakowski
*Assistant Examiner*—Timothy J. Kugel
(74) *Attorney, Agent, or Firm*—Oblon, Spivak, McClelland, Maier & Neustadt, P.C.

(57) ABSTRACT

The invention relates to a mixture, comprising (A) 10 to 90 wt. % of at least one $C_6$ to $C_{18}$ alkyl ester, or $C_5$ to $C_8$ cycloalkyl ester of 2-cyano-3,3-diphenylacrylic acid and (B) 90 to 10 wt. % of at least one further compound, with at least one UV absorption maximum in the range 280 to 450 nm and structurally different from compound (A). Said mixture is suitable for the protection of human skin from damaging UV radiation and for the protection of coloured textile materials from colour fading.

26 Claims, No Drawings

UV ABSORBING MIXTURE WITH TEXTILE FIBER AFFINITY

The present invention relates to a mixture comprising
(A) from 10 to 90% by weight of at least one $C_6$- to $C_{18}$-alkyl ester or $C_5$- to $C_8$-cycloalkyl ester of 2-cyano-3,3-diphenylacrylic acid and
(B) from 90 to 10% by weight of at least one further compound which has at least one UV absorption maximum in the range from 280 to 450 nm and is structurally different from said compounds (A).

The present invention further relates to the use of this mixture as UV absorbers possessing affinity for textile fiber, to a method of protecting human skin against harmful UV radiation and a method of protecting dyed textile material against fading, to a method of increasing the UV protection factor UPF of textile material, to a laundry detergent and a laundry pre- and aftertreatment which include this UV absorber mixture possessing fiber affinity and also to textile material comprising this UV absorber mixture possessing fiber affinity.

The harmful effects on human skin of the UV content of sunlight are not restricted to premature skin aging and the formation of erythemas (skin reddening, sunburn). Excessively long and intensive exposure of the skin to UV radiation also raises the risk of developing skin cancer. The chief culprit responsible for skin reddening and the increased risk of skin cancer is the UV-B range of UV radiation, i.e., the range from about 280 to about 315 nm. The peak of the erythema action spectrum is located at 308 nm.

Textiles absorb UV radiation and so act as a physical barrier to protect the skin against the harmful effects of sunlight ("textile skin protection"). However, the skin-protecting effect of textiles is dependent on many factors such as fiber type, fabric construction, fabric weight, color, moisture content or nature of finish. Summer clothing in the form of lightweight and light-colored cotton textiles offers only slight and hence inadequate protection against UV radiation.

An excessive dose of UV radiation can not only cause skin damage, but is also crucially responsible for the fading of colored textiles which is induced by sunlight. There is therefore considerable interest in protecting colored textiles as well as human skin against the harmful effects of UV radiation.

It is mainly customary optical brighteners which have hitherto been used to finish and protect the textiles themselves and also for textile skin protection, especially stilbene- and triazine-based optical brighteners as described for example in EP-A 682 145, GB-A 2 313 375 or EP-A 728 749. But the agents are still in need of improvement with regard to their efficacy and possess a number of disadvantages. Significant disadvantages are their poor formulatability and their inadequate solubility in the respective application medium.

WO 97/44422 discloses that sunscreens especially from the group consisting of phenylbenzotriazoles, dibenzoylmethanes, p-aminobenzoic esters, cinnamic esters, salicylic esters, nitrogen-free 2-hydroxybenzophenones, phenylbenzimidazoles and 2-cyano-3,3-diphenylacrylic esters and also mixtures thereof—without the respective mixing ratios being specified, however—are able to protect dyed textile material against fading. 2-Cyano-3,3-diphenylacrylic esters exemplified are the 2-ethyl and 2-ethylhexyl esters. Experimental examples are described using 2-ethylhexyl 4-methoxycinnamate (Parsol® MCX) and 2-(2'-hydroxy-3',5'-di-tert-amylphenyl)-2H-benzotriazole (Tinuvin® 328).

WO 96/03486 describes essentially the same sunscreens as mentioned in WO 97/44422 as agents for protecting dyed textile material against fading. But these agents are likewise still in need of improvement with regard to their efficacy and possess a number of disadvantages.

It is an object of the present invention to provide fiber affinity UV absorber systems which are improved in their efficacy and which are free of the disadvantages of the prior art.

We have found that this object is achieved by the mixture of the compounds (A) and (B) defined at the beginning.

The $C_6$- to $C_{18}$-alcohol radical in the esters (A) can be linear or singly or multiply branched, and it can be of natural or synthetic origin. Such alcohols can be for example fatty alcohols, oxo alcohols, Ziegler alcohols or Guerbet alcohols. Typical examples of such compounds (A) are n-hexyl, n-heptyl, n-octyl, 2-ethylhexyl, n-nonyl, isononyl, n-decyl, n-dodecyl, n-tridecyl, isotridecyl, n-tetradecyl, n-pentadecyl, n-hexadecyl, n-heptadecyl, n-octadecyl or eicosyl ester. It is also possible for unsaturated alcohol radicals such as the oleyl, linolyl or linolenyl radical to occur. Mixtures of such esters can also be present.

As $C_5$- to $C_8$-cycloalkanol radicals in the esters (A) there may be mentioned for example cyclopentyl, 2- or 3-methylcyclopentyl, cyclohexyl, 2-, 3- or 4-methylcyclohexyl, dimethylcyclohexyl, cycloheptyl or cyclooctyl radicals.

Preference is given to linear or singly or multiply branched $C_8$- to $C_{13}$-alkyl esters of 2-cyano-3,3-diphenylacrylic acid. The corresponding 2-ethylhexyl ester is commercially available as Uvinul® N-539 T from BASF Aktiengesellschaft.

Great importance attaches to the mixing ratio of the compounds (A) with the compounds (B). Each of the two components has to be present in the mixture of the invention in a fraction of at least 10% by weight. Preference is given to a mixture of 20–80% by weight of (A) and 80–20% by weight of (B), especially 30–70% by weight of (A) and 70–30% by weight of (B), in particular 40–60% by weight of (A) and 60–40% by weight of (B).

Useful compounds (B) are usually commercially available sunscreens which have at least one UV absorption maximum in the range from 280 to 450 nm and are structurally different from the compounds (A).

In a preferred embodiment, the mixture of the invention contains such compounds (B) as have at least one UV absorption maximum in the range from 330 to 380 nm.

In a further preferred embodiment, the mixture of the invention contains such compounds (B) as have at least one UV absorption maximum in the range from 280 to 315 nm (UV-B range) with an $E^1_1$ value of at least 200, especially at least 250, and at least one UV absorption maximum in the range from 315 to 400 nm (UV-A range) with an $E^1_1$ value of at least 200, especially at least 250.

Sunscreens such as the compounds (B) have one or more bands in the UV absorption spectrum. For the purposes of the present invention, UV absorption maxima are the bands (measured in customary organic solvents such as dichloromethane or methanol at room temperature) which are associated with the corresponding local or absolute maxima in the UV spectrum of the respective compound.

The $E^1_1$ value indicates the absorbance of the compound (B) in solution at a concentration of 1% by weight and a pathlength of 1 cm. The solvent used for this measurement is usually dichloromethane, but the use of other solvents customary for such UV measurements does not produce fundamentally different values.

In a further preferred embodiment, the mixture of the invention contains such compounds (A) and such compounds (B) as form a common homogeneous liquid phase in the temperature range from 10 to 35° C. without solvents or diluents being added. This common homogeneous liquid phase can usually be considered a solution of one of the components in the other. The advantage of such homogeneous mixtures is especially their convenience of production and application.

In a further preferred embodiment, the mixture of the invention contains such compounds (B) as have an n-octanol/water partition coefficient log P of at least 1.9, especially at least 2.5, in particular at least 3.3. Log P can be determined experimentally or by calculation. Both procedures are described in Chemical Reviews Volume 71, No. 5, pages 52-5-616 (1971).

The compounds (B) are preferably selected from the group consisting of
- (a) phenylbenzotriazoles,
- (b) dibenzoylmethanes,
- (c) esters of p-aminobenzoic acid,
- (d) esters of cinnamic acid,
- (e) esters of salicylic acid,
- (f) nitrogen-free 2-hydroxybenzophenones,
- (g) phenylbenzimidazoles,
- (h) acrylates that are structurally different from the compounds (A),
- (i) diarylbutadienes,
- (j) amino-substituted hydroxybenzophenones and
- (k) triazines.

Typical UV-absorbing phenylbenzotriazoles (a) are:
2,2'-hydroxy-5-methylphenylbenzotriazole,
2,2'-hydroxy-5-tert-octylphenylbenzotriazole,
2-hydroxy-3-sec-butyl-5-tert-butylbenzotriazole (Tinuvin® 350),
2-hydroxy-3-dodecyl-5-methylphenylbenzotriazole (Tinuvin® 571),
2-(2H-benzotriazol-2-yl)-4-methylphenol (Tinuvin® P),
2-(2H-benzotriazol-2-yl)-4-n-octylphenyl (Tinuvin® 329),
2-(2H-benzotriazol-2-yl)-4,6-di(2'-phenylisopropyl)phenol (Tinuvin® 234),
2-(2H-benzotriazol-2-yl)-4,6-di(tert-butyl)phenol (Tinuvin® 320),
2-(6-chloro-2H-benzotriazol-2-yl)-4-methyl-6-tert-butylphenol (Tinuvin® 326),
2-(6-chloro-2H-benzotriazol-2-yl)-2,6-di-tert-butylphenol (Tinuvin® 327),
2-(2'-hydroxy-3',5'-di-tert-amylphenyl)-2H-benzotriazole (Tinuvin® 328),
mixture of polyoxyethylene glycol β-[3-(2H-benzotriazol-2-yl)-5-tert-butyl-4-hydroxyphenyl] propionate and polyoxyethylene glycol bis-β-[3-(2H-benzotriazol-2-yl)-5-tert-butyl-4-hydroxyphenyl]propionate having an average molecular weight >600 (Tinuvin® 1130),
cocoyl-2-[2'-hydroxy-3'-(cocoyl dimethylbutanoate)-5'-methylphenyl]benzotriazole,
cocoyl 3-[3'-(2H-benzotriazol-2'-yl)-5-tert-butyl-4'-hydroxyphenyl]propionate,
2,2'-methylenebis-[6-(2H-benzotriazol-2-yl)-4-(1,1,3,3-tetramethylbutyl)]phenol (Tinuvin® 360),
2-(2H-1,2,3-benzotriazol-2-yl)-4-methyl-6-(2-methyl-3-{1,3,3,3-tetramethyl-1-[(trimethylsilyl)oxy] disiloxanyl}propyl)phenol.

Typical UV-absorbing dibenzoylmethanes (b) are:
3-(4-isopropylphenyl)-3-phenylpropane-1,3-dione (Eusolex® 8020),
1-(4-tert-butylphenyl)-3-(4-methoxyphenyl)propane-1,3-dione (Uvinul® BMBM),
1,3-bis-(4-methoxyphenyl)propane-1,3-dione.

Typical UV-absorbing esters of p-aminobenzoic acid (c) are:
ethyl 4-bis-(hydroxypropyl)aminobenzoate (Amerscheen® P),
2,3-dihydroxypropyl 4-aminobenzoate (Nipa® GMPA),
menthyl 2-aminobenzoate (Sunarome® UVA),
2-ethylhexyl 4-dimethylaminobenzoate (Escalol® 507),
amyl 4-dimethylaminobenzoate,
ethyl 4-dimethylaminobenzoate,
butyl 4-dimethylaminobenzoate,
octyl 4-dimethylaminobenzoate,
lauryl 4-dimethylaminobenzoate,
oleyl 4-dimethylaminobenzoate,
polyethoxyethyl 4-bis-(polyethoxy)-4-aminobenzoate (Uvinul® P-25), N-propoxylated ethyl 4-aminobenzoate.

Typical UV-absorbing esters of cinnamic acid (d) are:
2-ethylhexyl 4-methoxycinnamate (Uvinul® MC80, Parsol® MCX),
2-ethoxyethyl 4-methoxycinnamate,
propyl 4-methoxycinnamate,
isoamyl 4-methoxycinnamate,
cyclohexyl 4-methoxycinnamate,
isopropyl 4-methoxycinnamate,
octyl cinnamate,
ethyl 4-isopropylcinnamate,
ethyl α-cyano-β-phenylcinnamate,
2-ethylhexyl α-cyano-β-phenylcinnamate.

Typical UV-absorbing esters of salicylic acid (e) are:
2-ethylhexyl salicylate (Sunarome® WMO),
3,3,5-trimethylcyclohexyl 2-hydroxybenzoate,
3,3,5-trimethylcyclohexyl 2-acetamidobenzoate,
2-ethylhexyl 2-(4-phenylbenzoyl)benzoate,
4-isopropylbenzyl salicylate,
amyl salicylate,
menthyl salicylate,
homomethyl salicylate,
phenyl salicylate,
benzyl salicylate,
iso-decyl salicylate.

Typical UV-absorbing nitrogen-free 2-hydroxybenzophenones (f) are:
2-hydroxy-4-methoxybenzophenone (Uvinul® M40),
2,2'-dihydroxy-4-methoxybenzophenone (Spectra-Sorb® UV-24),
2,4-dihydroxybenzophenone (Uvinul® 3000),
2,2',4,4'-tetrahydroxybenzophenone (Uvinul® D-50),
2,2'-dihydroxy-4,4'-dimethoxybenzophenone (Uvinul® D-49),
2,2-dihydroxy-4,4-dimethoxybenzophenone (Uvinul® 3049),
2-hydroxy-4-(2-ethylhexyloxy)benzophenone,
2-hydroxy-4-(n-octyloxy)benzophenone (Uvinul® 3008),
2-hydroxy-4-methoxy-4'-methylbenzophenone (Mexenone®),
4-phenylbenzophenone,
2-ethylhexyl 4'-phenylbenzophenone-2-carboxylate,
2-hydroxy-3-carboxybenzophenone,
benzophenone-3 cocoyl acetate ether,
2-hydroxy-4-methoxybenzophenone-5-sulfonic acid (Uvinul® MS 40) and its sodium salt, 2,2'-dihydroxy-4,4,-dimethoxybenzophenone-5,5'-bissulfonic acid and its sodium salt (Uvinul® DS 49).

Typical UV-absorbing phenylbenzimidazoles (g) are:
2-phenylbenzimidazole-5-sulfonic acid (Eusolex® 232) and its potassium, sodium and triethanolamine salts,
2-[5,6-disulfo-(1H-benzimidazol-2-yl)phenyl]-1H-benzimidazole-5,6-disulfonic acid.

Typical UV-absorbing acrylates (h) that differ structurally from the compounds (A) are:
3-imidazol-4-ylacrylic acid,
ethyl 3-imidazol-4-yl acrylate,
2-cyano-3-(4-methoxyphenyl)acrylic acid,
hexyl 2-cyano-3-(4-methoxyphenyl) acrylate.

Typical UV-absorbing diarylbutadienes (i) are especially 4,4-diarylbutadienes of the formula I as are described in U.S. Pat. No. 6,093,385 for cosmetic and pharmaceutical preparations:

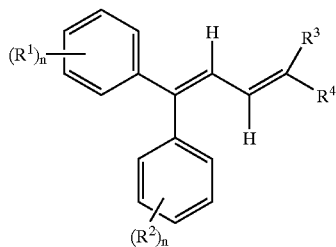

I where the diene system has the Z,Z; Z,E; E,Z or E,E configuration or a mixture thereof, and where the variables independently of one another have the following meanings:

$R^1$ and $R^2$
   hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted, substituents which confer solubility in water and are selected from the group consisting of carboxylate, sulfonate or ammonium radicals;

$R^3$ hydrogen, $COOR^5$, $COR^5$, $CONR^5R^6$, $CN$;
$R^4$ $COOR^6$, $COR^6$, $CONR^5R^6$;
$R^5$ hydrogen, $[X]_o$—$R^7$, $C_1$–$C_6$-alkylene-$SO_3Y$, $C_1$–$C_6$-alkylene-$PO_3Y$, $C_1$–$C_6$-alkylene-$N(R^8)_3{}^+A^-$;
$R^6$ $[X]_o$—$R^7$, $C_1$–$C_6$-alkylene-$SO_3Y$, $C_1$–$C_6$-alkylene-$PO_3Y$, $C_1$–$C_6$-alkylene-$N(R^8)_3{}^+A^-$;
X —$CH_2$—$CH_2$-Z-, —$CH_2$—$CH_2$—$CH_2$-Z-, —$CH(CH_3)$—$CH_2$-Z-, —$CH_2$—$CH_2$—$CH_2$—$CH_2$-Z-, —$CH_2$—$CH(CH_2$—$CH_3)$-Z-;
Cl, Br, I, $SO_4R^9$;
Y hydrogen, $Na^+$, $K^+$, $Mg^{2+}$, $Ca^{2+}$, $Li^+$, $Al^{3+}$, $N(R^8)_4{}^+$;
Z O, NH;
$R^7$ and $R^8$
   hydrogen, $C_1$–$C_6$-alkyl, $C_2$–$C_6$-alkenyl, $C_1$–$C_6$-acyl;
$R^9$ hydrogen, $C_1$–$C_6$-alkyl, $C_2$–$C_6$-alkenyl;
n 1 to 3;
o 1 to 150.

With regard to a more particular specification of the structures of the 4,4-diarylbutadienes of the formula I and examples of such compounds I, the disclosure in U.S. Pat. No. 6,093,385 is expressly incorporated herein by reference. A typical example of a representative of such a compound (i) is 1,1-bis(neopentyloxycarbonyl)-4,4-diphenyl-1,3-butadiene.

Typical UV-absorbing amino-substituted hydroxybenzophenones (I) are in particular those of the formula II as are described in U.S. Pat. No. 6,409,995 for cosmetic and pharmaceutical preparations:

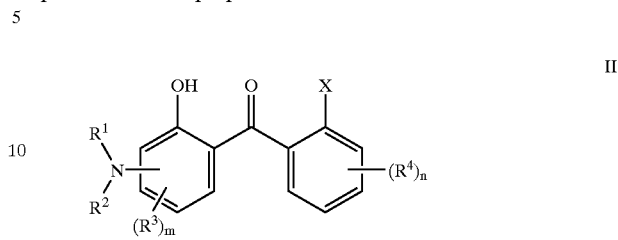

II in which the variables independently of one another have the following meanings:

$R^1$ and $R^2$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, where the substituents $R^1$ and $R^2$ together with the nitrogen atom to which they are bonded can form a 5- or 6-membered ring;

$R^3$ and $R^4$ are $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, heteroaryl, optionally substituted, substituents which confer solubility in water and are selected from the group consisting of a nitrile group, carboxylate, sulfonate or ammonium radicals;

x is hydrogen, $COOR^5$, $CONR^6R^7$;
$R^5$ to $R^7$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, —(Y—O)$_o$—Z, aryl;
Y is —$(CH_2)_2$—, —$(CH_2)_3$—, —$(CH_2)_4$—, —$CH(CH_3)$—$CH_2$—;
Z is —$CH_2$—$CH_3$, —$CH_2$—$CH_2$—$CH_3$, —$CH_2$—$CH_2$—$CH_2$—$CH_3$, —$CH(CH_3)$—$CH_3$;
m is from 0 to 3;
n is from 0 to 4;
o is from 1 to 20.

With regard to a more particular specification of the structures of the amino-substituted hydroxybenzophenones of the formula II and examples of such compounds II, the disclosure in U.S. Pat. No. 6,409,995 is expressly incorporated herein by reference. A typical example of a representative of such a compound (j) is n-hexyl 2-(4'-diethylamino-2'-hydroxybenzoyl)-benzoate.

The UV absorbers from the group of the diarylbutadienes (i) and of the amino-substituted hydroxybenzophenones (j) are each also useful alone as textile fiber affinity UV absorbers on textile material to protect human skin against harmful UV radiation and/or to protect dyed textile material against fading. The statements hereinbelow with regard to the applications of the mixture according to the invention apply equally to the diarylbutadienes (i) and the amino-substituted hydroxybenzo-phenomes (j) alone.

Typical UV-absorbing triazines (k) are:
2,4,6-trianilino-4-(carbo-2'-ethylhexyl-1'-oxy)-1,3,5-triazine (Uvinul® T-150),
2-ethylhexyl 4-{[4-{4-[tert-butylamino)carbonyl]anilino}-6-(4-{[2-ethylhexyl)oxy]carbonyl}anilino)-1,3,5-triazin-2-yl]amino}benzoate,
2-(4-methoxyphenyl)-4,6-di-[4-(2-ethylhexyloxy)-2-hydroxyphenyl]-1,3,5-triazine.

Representatives of the compounds (B) of the type (a) to (h) and (k) are incidentally described in WO 97/44422 and WO 96/03486.

As well as compounds of type (a) to (k), useful compounds (B) further include for example the following:
3-(4-methylbenzylidene)bornan-2-one (Eusolex® 6300),
5-(3,3-dimethyl-2-norbornylidene)-3-penten-2-one,
3-benzylidenebornan-2-one,
digalloyl trioleate,
2-hydroxy-1,4-naphthalenedione,
5-methyl-2-phenylbenzoxazole,
dibenzaldehydeamine,
dianisoylmethane,
methyleugenol,
2-amino-6-hydroxypurine,
N-(4-ethoxycarbonylphenyl)-N'-methyl-N'-phenylformamidine (Givosorb® UV1),
N-(4-ethoxycarbonylphenyl)-N'-ethyl-N'-phenylformamidine (Givosorb® UV2),
3-(4'-methylbenzylidene)camphor (Uvinul® MBC95),
$N^1$-(2-ethoxyphenyl)-$N^2$-(2-ethylphenyl)ethanediamide,
$N^1$-(2-ethoxyphenyl)-$N^2$-(4-dodecaphenyl)ethanediamide,
2-ethylhexyl 2-cyano-(3-oxo-2,3-dihydro-1H-isoindol-1-ylidene)-ethanoate,
1,1-dicyano-2-(4-butyloxy)phenyl-2-phenylethene.

It may occasionally be of advantage for the inventive mixture of components (A) and (B) to contain antioxidants and/or free-radical traps or to be used together with these in its use as UV absorbers possessing textile fiber affinity.

Antioxidants and free-radical traps which may be used here include all customary compounds of this type, but in particular:
substituted phenols, hydroquinones and pyrocatechols such as 2,6-di-tert-butylphenol, 2,4,6-tri-tert-butylphenol, 2,4-dimethyl-6-tert-butylphenol, 2,6-di-tert-butyl-4-methyl-phenol, 2,6-di-tert-butyl-4-methoxyphenol, 3-tert-butyl-4-methoxyphenol, 2,2'-methylenebis(4-methyl-6-tert-butylphenol), propyl, octyl and dodecyl gallate or tert-butylhydroquinone
ascorbic, lactic, citric and tartaric acid and salts thereof
tocopherol (acetyl-α-tocopherol)
diazobicyclo[2,2,2]octane
customary aromatic amines
customary organic sulfides
customary sterically hindered amines such as Uvinul® 4049H, Uvinul® 4050H and Uvinul® 5050H (marketed by BASF Aktiengesellschaft).

The inventive mixture of components (A) and (B) is very useful as a UV absorber mixture possessing textile fiber affinity. On the one hand, the inventive mixture, when applied to a textile material, protects the human skin against harmful UV radiation. On the other, the inventive mixture protects dyed textile material against fading. The two protective effects preferably occur simultaneously.

Textile material for which the mixture of the present invention possesses affinity and on which it is able to develop its protective action includes in particular clothing articles, i.e., textiles which are worn on the human skin, but also house and garden articles comprising dyed textiles such as awnings and sunshades which are exposed to intensive solar irradiation. This textile material to be protected preferably comprises cellulose (cotton), examples of textile materials of interest here being apparel textiles comprising cotton or cotton-polyester blends.

The present invention also provides a method of protecting human skin against harmful UV radiation, which comprises applying the mixture of the invention to textile material in the course of textile finishing, i.e., in the course of the manufacture of the textiles.

The present invention further provides a method of protecting human skin against harmful UV radiation, which comprises applying the mixture of the invention to textile material in the course of laundering and/or laundry pre- or aftertreatment.

The present invention further provides a method of protecting dyed textile material against fading, which comprises applying the mixture of the invention to textile material in the course of textile finishing, i.e., in the course of the manufacture of the textiles.

The present invention further provides a method of protecting dyed textile material against fading, which comprises applying the mixture of the invention to textile material in the course of laundering and/or laundry pre- or aftertreatment.

The present invention further provides a method of increasing the UV protection factor UPF of textile material, which comprises applying the mixture of the invention to textile material in the course of textile finishing i.e., in the course of the manufacture of the textiles.

The present invention further provides a method of increasing the UV protection factor UPF of textile material, which comprises applying the mixture of the invention to textile material in the course of laundering and/or laundry pre- or aftertreatment.

The UV protection factor UPF of textiles is determined in accordance with the Australian/New Zealand standard AS/NZS 4399:1996 using an in vitro method. It measures the UV transmission of the textile object. The spectral transmission can be used to determine the protection factor directly using the following equation:

$$UPF = \frac{\int_{\lambda=280\ nm}^{400\ nm} S_\lambda \times E_\lambda \times d\lambda}{\int_{\lambda=280\ nm}^{400\ nm} S_\lambda \times E_\lambda \times T_\lambda \times d\lambda}$$

where
$S_\lambda$=spectral irradiation of the sun in the UV region at the wavelength λ
$E_\lambda$=spectral erythema action of the UV radiation at the wavelength λ
$T_\lambda$=spectral transmission of the textile object at the wavelength λ.

The mixture of the invention can be applied in the course of the finishing of the textile material, i.e., in the course of the manufacture of the textiles, or in the course of caring for the finished textile article, i.e., in the course of laundering and/or laundry pre- or aftertreatment.

By textile finishing are meant the operations carried out in the course of the manufacture of textiles to enhance the utility of the textiles and make them more attractive through advantageous manipulation of their external properties. Typical operations to enhance utility are easycare finishing, creaseproofing and shrinkproofing. Typical processes to enhance attractiveness are dyeing, bleaching, printing and mercerizing. The finishing of piece goods in particular generally involves the use of hand modifiers which include the finishing agents and to which the mixture of the present invention is preferably likewise added.

The present invention also provides a laundry detergent comprising from 0.01 to 20% by weight, in particular from 0.1 to 10% by weight, especially from 0.1 to 5% by weight, of an inventive mixture of components (A) and (B) as well as other, customary ingredients. In this connection, the components (A) and (B) can in principle be added separately to the formulation, or a ready-prepared mixture of (A) and (B) can be incorporated into the formulation; the latter method will be the better one in many cases, especially when (A) and (B) form a common homogeneous liquid phase in the temperature range from 10 to 35° C. without solvents or diluents being added.

The laundry detergent of the invention generally includes as other, customary ingredients
(B) from 1 to 60% by weight of inorganic builders based on crystalline or amorphous aluminosilicates, crystalline or amorphous silicates, carbonates or phosphates,
(C) from 0.5 to 40% by weight of anionic surfactants, and
(D) from 0.5 to 40% by weight of nonionic surfactants.

Suitable inorganic builders (B) are especially crystalline or amorphous aluminosilicates having ion-exchanging properties such as, in particular, zeolites. Various types of zeolite are suitable, especially zeolites A, X, B, P, MAP and HS in their sodium form or in forms in which sodium is partly replaced by other cations such as lithium, potassium, calcium, magnesium or ammonium. Suitable zeolites are described for example in EP-A 038591, EP-A 021491, EP-A 087035, U.S. Pat. No. 4604224, GB-A 2013259, EP-A 522726, EP-A 384070 and WO-A 94/24251.

Suitable crystalline silicates (B) are for example disilicates or sheet-silicates, for example $\delta$-$Na_2Si_2O_5$ or $\beta$-$Na_2Si_2O_5$ (SKS 6 or SKS 7 from Hoechst). The silicates can be used in the form of their alkali metal, alkaline earth metal or ammonium salts, preferably as sodium, lithium and magnesium silicates.

Amorphous silicates such as, for example, sodium metasilicate, which has a polymeric structure, or amorphous disilicate (Britesil® H 20 from Akzo) are likewise useful.

Suitable inorganic builder substances (B) based on carbonate are carbonates and bicarbonates. These can be used in the form of their alkali metal, alkaline earth metal or ammonium salts. Preference is given to using sodium, lithium and magnesium carbonates or bicarbonates, especially sodium carbonate and/or sodium bicarbonate.

Customary phosphates useful as inorganic builders (B) are polyphosphates, such as, for example, pentasodium triphosphate.

The components (B) mentioned can be used singly or mixed with each or one another.

The component (B) is preferably present in the laundry detergent of the invention in an amount from 5 to 50% by weight, especially from 10 to 45% by weight.

In a preferred embodiment, the laundry detergent of the invention includes no phosphate-based builders or not more than 5% by weight, especially not more than 2% by weight, of phosphate-based builders.

Suitable anionic surfactants (C) are for example fatty alcohol sulfates of fatty alcohols containing from 8 to 22, preferably from 10 to 18, carbon atoms, e.g., $C_9$- to $C_{11}$-alcohol sulfates, $C_{12}$- to $C_{14}$-alcohol sulfates, $C_{12}$–$C_{18}$-alcohol sulfates, lauryl sulfate, cetyl sulfate, myristyl sulfate, palmityl sulfate, stearyl sulfate and tallow alcohol sulfate.

Further suitable anionic surfactants are sulfated ethoxylated $C_8$- to $C_{22}$-alcohols (alkyl ether sulfates) and their soluble salts. Compounds of this kind are prepared for example by first alkoxylating a $C_8$- to $C_{22}$-alcohol, preferably a $C_{10}$- to $C_{18}$-alcohol, for example a fatty alcohol, and subsequently sulfating the alkoxylation product. The alkoxylation is preferably carried out using ethylene oxide, from 1 to 50, preferably from 1 to 20, mol of ethylene oxide being used per mole of alcohol. However, the alkoxylation of the alcohols can also be effected with propylene oxide alone and optionally butylene oxide. Also suitable are those alkoxylated $C_8$- to $C_{22}$-alcohols which contain ethylene oxide and propylene oxide or ethylene oxide and butylene oxide or ethylene oxide and propylene oxide and butylene oxide. The alkoxylated $C_8$- to $C_{22}$-alcohols can contain the ethylene oxide, propylene oxide and butylene oxide units in the form of blocks or in random distribution. Depending on the type of alkoxylation catalyst, alkyl ether sulfates can be obtained with broad or narrow alkylene oxide homolog distribution.

Further suitable anionic surfactants are alkanesulfonates such as $C_8$- to $C_{24}$-alkanesulfonates, preferably $C_{10}$- to $C_{18}$-alkanesulfonates, and also soaps such as, for example, the sodium and potassium salts of $C_8$- to $C_{24}$-arboxylic acids.

Further suitable anionic surfactants are linear $C_8$- to $C_{20}$-alkylbenzenesulfonates ("LAS"), preferably linear $C_9$- to $C_{13}$-alkylbenzenesulfonates and -alkyltoluenesulfonates.

Useful anionic surfactants (C) further include $C_8$- to $C_{24}$-Olefinsulfonates and -disulfonates, which may also be mixtures of alkene- and hydroxyalkane-sulfonates and -disulfonates, respectively, alkyl ester sulfonates, sulfonated polycarboxylic acids, alkylglycerolsulfonates, fatty acid glyceryl ester sulfonates, alkylphenol polyglycol ether sulfates, paraffinsulfonates containing from about 20 to about 50 carbon atoms (based on paraffin or paraffin mixtures obtained from natural sources), alkyl phosphates, acyl isethionates, acyl taurates, acyl methyltaurates, alkylsuccinic acids, alkenylsuccinic acids or their monoesters or monoamides, alkylsulfosuccinic acids or their amides, mono- and diesters of sulfosuccinic acids, acyl sarcosinates, sulfated alkylpolyglucosides, alkylpolyglycol carboxylates and also hydroxyalkyl sarcosinates.

The anionic surfactants are preferably included in the laundry detergent in the form of salts. Suitable cations in these salts are alkali metal ions such as sodium, potassium and lithium and ammonium salts, for example hydroxyethylammonium, di(hydroxyethyl) ammonium and tri (hydroxyethyl) ammonium salts.

The component (C) is preferably present in the laundry detergent of the invention in an amount of from 1 to 30% by weight, in particular from 3 to 25% by weight, especially from 5 to 15% by weight. If linear $C_9$- to $C_{20}$-alkylbenzenesulfonates (LAS) are used, they are customarily used in an amount of up to 10% by weight, especially up to 8% by weight.

It is possible to use individual anionic surfactants or a combination of different anionics. It is possible to use anionic surfactants from just one class, for example just fatty alcohol sulfates or just alkylbenzenesulfonates, but it is also possible to use surfactant mixtures from different classes, for example a mixture of fatty alcohol sulfates and alkylbenzenesulfonates.

Examples of suitable nonionic surfactants (D) are alkoxylated C8- to $C_{22}$-alcohols such as fatty alcohol alkoxylates or oxo alcohol alkoxylates. The alkoxylation can be carried out with ethylene oxide, propylene oxide and/or butylene oxide. Useful surfactants include all alkoxylated alcohols which contain at least two molecules of an aforementioned alkylene oxide after an addition reaction. Here too block polymers of ethylene oxide, propylene oxide and/or butylene oxide are suitable or addition products which contain the alkylene oxides mentioned in random distribution. The amount of alkylene oxide used per mole of alcohol is from 2 to 50, preferably from 3 to 20, mol of at least one alkylene oxide. The preferred alkylene oxide is ethylene oxide. The alcohols preferably have from 10 to 18 carbon atoms.

Depending on the type of alkoxylation catalyst, alkoxylates can be obtained with broad or narrow alkylene oxide homolog distribution.

A further class of suitable nonionic surfactants are alkylphenol alkoxylates such as alkylphenol ethoxylates containing $C_6$- to $C_{14}$-alkyl chains and from 5 to 30 mol of alkylene oxide units.

Another class of nonionic surfactants are alkylpolyglucosides having from 8 to 22, preferably from 10 to 18, carbon atoms in the alkyl chain. These compounds usually contain from 1 to 20, preferably from 1.1 to 5, glucoside units.

Another class of nonionic surfactants are N-alkylglucamides of the general structures

where $B_1$ is $C_6$- to $C_{22}$-alkyl, $B^2$ is hydrogen or $C_1$- to $C_4$-alkyl and D is a polyhydroxyalkyl radical containing from 5 to 12 carbon atoms and at least 3 hydroxyl groups. Preferably, $B^1$ is $C_{10}$- to $C_{18}$-alkyl, $B^2$ is $CH_3$ and D is a $C_5$ or $C_6$ radical. Such compounds are obtained for example by acylating reductively aminated sugars with acyl chlorides of $C_{10}$- to $C_{18}$-carboxylic acids.

Further suitable nonionic surfactants are the end group capped fatty acid amide alkoxylates known from WO-A 95/11225 which have the general formula

where
$R^1$ is $C_5$- to $C_{21}$-alkyl or -alkenyl,
$R^2$ is $C_1$- to $C_4$-alkyl,
$A^1$ is $C_2$- to $C_4$-alkylene,
y is 2 or 3, and
x is from 1 to 6.

Examples of such compounds are the reaction products of n-butyltriglycolamine of the formula $H_2N—(CH_2—CH_2—O)_3—C_4H_9$ with methyl dodecanoate or the reaction products of ethyltetraglycolamine of the formula $H_2N—(CH_2—CH_2—O)_4—C_2H_5$ with a commercially available mixture of saturated methyl esters of $C_8$- to $C_{18}$-fatty acids.

Useful nonionic surfactants (D) further include block copolymers of ethylene oxide, propylene oxide and/or butylene oxide (Pluronic® and Tetronic® products from BASF), polyhydroxy or polyalkoxy fatty acid derivatives such as polyhydroxy fatty acid amides, N-alkoxy- or N-aryloxy-polyhydroxy fatty acid amides, fatty acid amide ethoxylates, especially end group capped ones, and also fatty acid alkanolamide alkoxylates.

The component (D) is preferably present in the laundry detergent of the invention in an amount of from 1 to 30% by weight, especially from 3 to 25% by weight, in particular from 5 to 20% by weight.

Individual nonionic surfactants or a combination of different nonionics can be used. It is possible to use nonionic surfactants from just one class, especially just alkoxylated $C_8$- to $C_{22}$-alcohols, but it is also possible to use surfactant mixtures from different classes.

In a preferred embodiment, the laundry detergent of the invention, in addition to the inorganic builders (B), includes from 0.05 to 20% by weight, especially from 1 to 10% by weight, of organic cobuilders in the form of low molecular weight, oligomeric or polymeric carboxylic acids, especially polycarboxylic acids, or phosphonic acids or their salts, especially sodium or potassium salts.

Examples of low molecular weight carboxylic acids or phosphonic acids useful as organic cobuilders are:

phosphonic acids such as, for example, 1-hydroxyethane-1,1-diphosphonic acid, aminotris(methylenephosphonic acid), ethylenediaminetetra(methylenephosphonic acid), hexamethylenediaminetetra(methylenephosphonic acid) and diethylenetriaminepenta(methylenephosphonic acid);

$C_4$- to $C_{20}$-di-, -tri- and -tetracarboxylic acids such as, for example, succinic acid, propanetricarboxylic acid, butanetetracarboxylic acid, cyclopentanetetracarboxylic acid and alkyl and alkenylsuccinic acids having $C_2$- to $C_{16}$-alkyl or -alkenyl moieties;

$C_4$- to $C_{20}$-hydroxycarboxylic acids such as, for example, malic acid, tartaric acid, gluconic acid, glutaric acid, citric acid, lactobionic acid and sucrose mono-, di- and tricarboxylic acid;

aminopolycarboxylic acids such as, for example, nitrilotriacetic acid, β-alaninediacetic acid, ethylenediaminetetraacetic acid, serinediacetic acid, isoserinediacetic acid, alkylethylene-diaminetriacetates, N,N-bis(carboxymethyl)glutamic acid, ethylenediaminedisuccinic acid and N-(2-hydroxyethyl)imino-diacetic acid, methyl- and ethylglycinediacetic acid.

Examples of oligomeric or polymeric carboxylic acids useful as organic cobuilders are:

oligomaleic acids as described for example in EP-A 451508 and EP-A 396303;

co- and terpolymers of unsaturated $C_4$–$C_8$-dicarboxylic acids which may contain copolymerized units derived from monoethylenically unsaturated comonomers of the group (i) in amounts of up to 95% by weight, of the group (ii) in amounts of up to 60% by weight, and of the group (iii) in amounts of up to 20% by weight.

Examples of unsaturated $C_4$–$C_8$-dicarboxylic acids useful here include maleic acid, fumaric acid, itaconic acid and citraconic acid. Maleic acid is preferred.

The group (i) consists of monoethylenically unsaturated $C_3$–$C_8$-monocarboxylic acids, for example acrylic acid, methacrylic acid, crotonic acid and vinylacetic acid. Preferred members of group (i) are acrylic acid and methacrylic acid.

Group (ii) consists of monoethylenically unsaturated $C_2$–$C_{22}$-olefins, vinyl alkyl ethers having $C_1$–$C_8$-alkyl groups, styrene, vinyl esters of $C_1$–$C_8$-arboxylic acids, (meth)acrylamide and vinylpyrrolidone. Preferred members of group (ii) are $C_2$–$C_6$-olefins, vinyl alkyl ethers containing $C_1$–$C_4$-alkyl groups, vinyl acetate and vinyl propionate.

Group (iii) consists of (meth)acrylic esters of $C_1$- to $C_8$-alcohols, (meth)acrylonitrile, (meth)acrylamides of $C_1$–$C_8$-amines, N-vinylformamide and N-vinylimidazole.

If the polymers of group (ii) contain units derived from vinyl esters, these units may also be partly or wholly hydrolyzed into vinyl alcohol units. Suitable co- and terpolymers are known for example from U.S. Pat. No. 3,887,806 and DE-A 4313909.

Copolymers of dicarboxylic acids useful as organic cobuilders are preferably:

copolymers of maleic acid and acrylic acid in a weight ratio of from 10:90 to 95:5, particularly preferably those in a weight ratio of from 30:70 to 90:10 with molar masses from 1000 to 150,000;

terpolymers of maleic acid, acrylic acid and a vinyl ester of a $C_1$–$C_3$-carboxylic acid in a weight ratio of from 10 (maleic acid): 90 (acrylic acid+vinyl ester) to 95 (maleic acid):10 (acrylic acid+vinyl ester), the weight ratio of acrylic acid to vinyl ester being variable within the range from 30:70 to 70:30;

copolymers of maleic acid with $C_2$–$C_8$-olefins in a molar ratio of from 40:60 to 80:20, of which copolymers of maleic acid with ethylene, propylene or isobutene in a molar ratio of 50:50 are particularly preferred.

Graft polymers of unsaturated carboxylic acids on low molecular weight carbohydrates or hydrogenated carbohydrates, cf. U.S. Pat. No. 5,227,446, DE-A 4415623 and DE-A 4313909, are likewise useful as organic cobuilders.

Examples of useful unsaturated carboxylic acids here are maleic acid, fumaric acid, itaconic acid, citraconic acid, acrylic acid, methacrylic acid, crotonic acid and vinylacetic acid and also mixtures of acrylic acid and maleic acid which are grafted on in amounts of from 40 to 95% by weight, based on the component to be grafted.

The graft copolymer may additionally include, by way of modification, up to 30% by weight, based on the component to be grafted, of further monoethylenically unsaturated monomers in copolymerized form. Suitable modifying monomers are the abovementioned monomers of groups (ii) and (iii).

Useful grafting bases include degraded polysaccharides, for example acidic or enzymatically degraded starches, inulins or cellulose, protein hydrolyzates and reduced (hydrogenated or reductively aminated) degraded polysaccharides, for example mannitol, sorbitol, aminosorbitol and N-alkylglucamine, and also polyalkylene glycols having molar masses of up to $M_W$=5000, for example polyethylene glycols, ethylene oxide/propylene oxide or ethylene oxide/butylene oxide or ethylene oxide/propylene oxide/butylene oxide block copolymers and alkoxylated mono- or polyhydric $C_1$–$C_{22}$-alcohols; cf. U.S. Pat. No. 5,756,456.

Polyglyoxylic acids useful as organic cobuilders are described for example in EP-B 001004, U.S. Pat. No. 5,399,286, DE-A 4106355 and EP-A 656914. The end groups of the polyglyoxylic acids can have different structures.

Polyamidocarboxylic acids and modified polyamidocarboxylic acids useful as organic cobuilders are known for example from EP-A 454126, EP-B 511037, WO-A 94/01486 and EP-A 581452.

Useful organic cobuilders also include in particular polyaspartic acids or cocondensates of aspartic acid with further amino acids, $C_4$–$C_{25}$-mono- or -dicarboxylic acids and/or $C_4$–$C_{25}$-mono- or -diamines. Particular preference is given to polyaspartic acids prepared in phosphorus-containing acids and modified with $C_6$–$C_{22}$-mono- or -dicarboxylic acids or with $C_6$–$C_{22}$-mono- or diamines.

Useful organic cobuilders further include iminodisuccinic acid, oxydisuccinic acid, aminopolycarboxylates, alkylpolyamino-carboxylates, aminopolyalkylenephosphonates, polyglutamates, hydrophobic modified citric acid, e.g., agaricic acid, poly-α-hydroxyacrylic acid, N-acylethylenediaminetriacetates such as lauroylethylenediaminetriacetate and alkylamides of ethylenediaminetetraacetic acid such as EDTA-tallowamide.

It is also possible to use oxidized starches as organic cobuilders.

In a further preferred embodiment, the laundry detergent of the invention, as well as in particular the inorganic builders (B), the anionic surfactants (C) and/or the nonionic surfactants (D), further includes from 0.5 to 20% by weight, especially from 1 to 10% by weight, of glycine-N,N-diacetic acid derivatives as described in WO 97/19159.

In a further preferred embodiment, the laundry detergent of the invention further comprises from 0.5 to 30% by weight, especially from 5 to 27% by weight, in particular from 10 to 23% by weight, of bleaching agents in the form of percarboxylic acids, e.g., diperoxododecanedicarboxylic acid, phthalimidopercaproic acid or monoperoxophthalic acid or -terephthalic acid, adducts of hydrogen peroxide with inorganic salts, for example sodium perborate monohydrate, sodium perborate tetrahydrate, sodium carbonate perhydrate or sodium phosphate perhydrate, adducts of hydrogen peroxide with organic compounds, for example urea perhydrate, or of inorganic peroxo salts, for example alkali metal persulfates, or alkali metal peroxodisulfates, optionally in combination with from 0 to 15% by weight, preferably from 0.1 to 15% by weight, especially from 0.5 to 8% by weight, of bleach activators. In the case of color detergents, the bleaching agent (if present) is generally used without bleach activator; in other cases, bleach activators are usually present.

Useful bleach activators include:

polyacylated sugars, for example pentaacetylglucose;

acyloxybenzenesulfonic acids and their alkali metal and alkaline earth metal salts, for example sodium p-nonanoyloxybenzenesulfonate or sodium p-benzoyloxybenzenesulfonate;

N,N-diacylated and N,N,N',N'-tetraacylated amines, for example N,N,N',N'-tetraacetylmethylenediamine and -ethylenediamine (TAED), N,N-diacetylaniline, N,N-diacetyl-p-toluidine or 1,3-diacylated hydantoins such as 1,3-diacetyl-5,5-dimethylhydantoin;

N-alkyl-N-sulfonylcarboxamides, for example N-methyl-N-mesylacetamide or N-methyl-N-mesylbenzamide;

N-acylated cyclic hydrazides, acylated triazoles or urazoles, for example monoacetylmaleic hydrazide;

O,N,N-trisubstituted hydroxylamines, for example O-benzoyl-N,N-succinylhydroxylamine, O-acetyl-N,N-succinylhydroxylamine or O,N,N-triacetylhydroxylamine;

N,N'-diacylsulfurylamides, for example N,N'-dimethyl-N,N'-diacetylsulfurylamide or N,N'-diethyl-N,N'-dipropionylsulfurylamide;

acylated lactams such as, for example, acetylcaprolactam, octanoylcaprolactam, benzoylcaprolactam or carbonylbiscaprolactam;

anthranil derivatives such as, for example, 2-methylanthranil or 2-phenylanthranil;

triacyl cyanurates, for example triacetyl cyanurate or tribenzoyl cyanurate;

oxime esters and bisoxime esters, for example O-acetylacetone oxime or bisisopropyl iminocarbonate;

carboxylic anhydrides, for example acetic anhydride, benzoic anhydride, m-chlorobenzoic anhydride or phthalic anhydride;

enol esters, for example isopropenyl acetate;

1,3-diacyl-4,5-diacyloxyimidazolines, for example 1,3-diacetyl-4,5-diacetoxyimidazoline;

tetraacetylglycoluril and tetrapropionylglycoluril;

diacylated 2,5-diketopiperazines, for example 1,4-diacetyl-2,5-diketopiperazine;

ammonium-substituted nitriles, for example N-methylmorpholiniumacetonitrile methylsulfate;

acylation products of propylenediurea and 2,2-dimethylpropylenediurea, for example tetraacetylpropylenediurea;

α-acyloxypolyacylmalonamides, for example α-acetoxy-N,N'-diacetylmalonamide;

diacyldioxohexahydro-1,3,5-triazines, for example 1,5-diacetyl-2,4-dioxohexahydro-1,3,5-triazine;

benz(4H)-1,3-oxazin-4-ones having alkyl radicals, for example methyl, or aromatic radicals, for example phenyl, in position 2.

The described bleaching system comprising bleaching agents and bleach activators may optionally include bleach catalysts as well. Examples of suitable bleach catalysts are quaternized imines and sulfoneimines, which are described for example in U.S. Pat. No. 5,360,569 and EP-A 453 003. Particularly effective bleach catalysts are manganese complexes, which are described for example in WO-A 94/21777. When used, such compounds are incorporated in laundry detergents at most in amounts up to 1.5% by weight, especially up to 0.5% by weight, and, in the case of very active manganese complexes, in amounts up to 0.1% by weight.

In addition to the described bleaching system comprising bleaching agents, bleach activators and optionally bleach catalysts, it is also possible for the laundry detergent of the invention to utilize systems involving enzymatic peroxide release or photoactivated bleaching systems.

In a further preferred embodiment, the laundry detergent of the invention additionally includes from 0.05 to 4% by weight of enzymes. Preferred laundry-detergent enzymes are proteases, amylases, lipases and cellulases. The enzymes are used in amounts which are preferably from 0.1 to 1.5% by weight, particularly preferably from 0.2 to 1.0% by weight, of the formulated enzyme. Examples of suitable proteases are Savinase and Esperase (from Novo Nordisk). An example of a suitable lipase is Lipolase (from Novo Nordisk). An example of a suitable cellulase is Celluzym (from Novo Nordisk). The use of peroxidases to activate the bleach system is also possible. Individual enzymes or a combination of different enzymes can be used. If desired, the laundry detergent of the invention may additionally include enzyme stabilizers, for example calcium propionate, sodium formate or boric acids or salts thereof, and/or antioxidants.

In addition to the main components heretofore mentioned, the laundry detergent of the invention may also include the following further customary additives in the amounts customary for this purpose:

cationic surfactants, customarily in an amount of up to 25% by weight, preferably from 3 to 15% by weight, for example $C_8$- to $C_{16}$-dialkyldimethylammonium halides, dialkoxydimethylammonium halides or imidazolinium salts with long-chain alkyl;

amphoteric surfactants, customarily in an amount of up to 15% by weight, preferably from 2 to 10% by weight, for example derivatives of secondary or tertiary amines, for example $C_{12}$–$C_{18}$-alkylbetaines or $C_{12}$–$C_{18}$-alkylsulfobetaines or amine oxides such as alkyldimethylamine oxides;

soil antiredeposition agents and soil release polymers (these are for example polyesters of polyethylene oxides with ethylene glycol and/or propylene glycol and aromatic dicarboxylic acids or aromatic and aliphatic dicarboxylic acids or polyesters of unilaterally end group capped polyethylene oxides with di- and/or more highly hydric alcohols and dicarboxylic acids. Such polyesters are known, cf. for example U.S. Pat. No. 3,557,039, GB-A-1 154 730, EP-A-0 185 427, EP-A-0 241 984, EP-A-0 241 985, EP-A-0 272 033 and U.S. Pat. No. 5,142,020. Further suitable soil release polymers are amphiphilic graft polymers or copolymers of vinyl ester and/or acrylic ester on polyalkylene oxides, cf. U.S. Pat. No. 4,746,456, U.S. Pat. No. 4,846,995, DE-A-3 711 299, U.S. Pat. No. 4,904,408, U.S. Pat. No. 4,846,994 and U.S. Pat. No. 4,849,126, or modified celluloses, for example methylcellulose, hydroxypropylcellulose, or carboxymethylcellulose. Soil antiredeposition agents and soil release polymers are present in the laundry detergents at from 0.1 to 2.5% by weight, preferably at from 0.2 to 1.5% by weight, particularly preferably at from 0.3 to 1.2% by weight. Preferred soil release polymers are the graft polymers of vinyl acetate on polyethylene oxide of molar mass 2500–8000 in a weight ratio of from 1.2:1 to 3.0:1 known from U.S. Pat. No. 4,746,456, and also commercially available polyethylene terephthalate/ polyoxyethylene terephthalates of molar mass 3000–25,000 from polyethylene oxides of molar mass 750–5000 with terephthalic acid and ethylene oxide and a molar ratio of polyethylene terephthalate to polyoxyethylene terephthalate of from 8:1 to 1:1 and the block polycondensates known from DE-A-44 03 866 which contain blocks of (a) ester units of polyalkylene glycols having a molar mass of from 500 to 7500 and aliphatic dicarboxylic acids and/or monohydroxymonocarboxylic acids and (b) ester units of aromatic dicarboxylic acids and polyhydric alcohols. These amphiphilic block copolymers have molar masses of from 1500 to 25,000.);

dye transfer inhibitors, for example homo- and copolymers of N-vinylpyrrolidone, of N-vinylimidazole, of N-vinyloxazolidone or of 4-vinylpyridine N-oxide with molar masses of from 15,000 to 100,000 and also crosslinked finely divided polymers based on these monomers and having a particle size of from 0.1 to 500, preferably from 0.1 to 250, $\mu$m;

nonsurfactant foam suppressants or foam inhibitors, for example organopolysiloxanes and mixtures thereof with microfine, optionally silanized silica and also paraffins, waxes, microwaxes and mixtures thereof with silanized silica;

complexing agents (also as organic cobuilders);

optical brighteners;

polyethylene glycols;

perfumes or fragrances;

fillers;

inorganic extenders, for example sodium sulfate;

formulation assistants;

solubility improvers;

opacifiers and pearlizers;

dyes;

corrosion inhibitors;

peroxide stabilizers;

electrolytes.

A solid laundry detergent according to the invention is customarily in powder or granule form or in the form of extrudates or tablets.

Pulverulent or granular laundry detergents according to the invention may include up to 60% by weight of inorganic extenders. Sodium sulfate is usually used for this purpose. However, the extender content of the laundry detergents of the invention is preferably low, only up to 20% by weight, particularly preferably only up to 8% by weight, especially in the case of compacts or ultracompacts. The solid laundry detergents of the invention may have various bulk densities in the range from 300 to 1300 g/l, especially within the range from 550 to 1200 g/l. Modern compacts generally have high bulk densities and a granular construction. To achieve the desired compaction of the detergents, it is possible to use the techniques customary in the art.

The laundry detergent of the invention is produced and optionally formulated in a conventional manner.

The present invention further provides a laundry pre- and aftertreatment comprising from 0.01 to 40% by weight, especially from 0.5 to 20% by weight, of an inventive mixture of components (A) and (B) as well as other, customary ingredients. In this connection, the components (A) and (B) can in principle be added separately to the formulation, or a ready-prepared mixture of (A) and (B) can be incorporated into the formulation; the latter method will be the better one in many cases, especially when (A) and (B) form a common homogeneous liquid phase in the temperature range from 10 to 35° C. without solvents or diluents being added.

Preference is here given to a textile pre- and aftertreatment further comprising from 1 to 50% by weight, especially from 3 to 30% by weight, of one or more cationic surfactants selected from the group consisting of quaternary diesterammonium salts, quaternary tetraalkylammonium salts, quaternary diamidoammonium salts, amidoamino esters and imidazolinium salts.

Quaternary diesterammonium salts are especially those which have two $C_{11}$- to $C_{22}$-alk(en)ylcarbonyloxy(mono- to pentamethylene) radicals and two $C_1$- to $C_3$-alkyl or -hydroxyalkyl radicals on the quaternary nitrogen atom and, for example, chloride, bromide, methosulfate or sulfate as counterion.

Quaternary diesterammonium salts further include in particular those which have a $C_{11}$- to $C_{22}$-alk(en)ylcarbonyloxytrimethylene radical bearing a $C_{11}$- to $C_{22}$-alk(en)ylcarbonyloxy radical on the central carbon atom of the trimethylene group and three $C_1$- to $C_3$-alkyl or -hydroxyalkyl radicals on the quaternary nitrogen atom and, for example, chloride, bromide, methosulfate or sulfate as counterion.

Quaternary tetraalkylammonium salts are in particular those which have two $C_1$- to $C_6$-alkyl radicals and two $C_8$- to $C_{24}$-alk(en)yl radicals on the quaternary nitrogen atom and, for example, chloride, bromide, methosulfate or sulfate as counterion.

Quaternary diamidoammonium salts are in particular those which have two $C_8$- to $C_{24}$-alk(en)ylcarbonylaminoethylene radicals, a substituent selected from hydrogen, methyl, ethyl and polyoxyethylene having up to 5 oxyethylene units and as fourth radical a methyl group on the quaternary nitrogen atom and, for example, chloride, bromide, methosulfate or sulfate as counterion.

Amidoamino esters are in particular tertiary amines bearing a $C_{11}$- to $C_{22}$-alk(en)ylcarbonylamino(mono- to trimethylene) radical, a $C_{11}$- to $C_{22}$-alk(en)ylcarbonyloxy(mono- to trimethylene) radical and a methyl group as substituents on the nitrogen atom.

Imidazolinium salts are in particular those which bear a $C_{14}$- to $C_{18}$-alk(en)yl radical in position 2 of the heterocycle, a $C_{14}$- to $C_{18}$-alk(en)ylcarbonyl(oxy or amino)ethylene radical on the neutral nitrogen atom and hydrogen, methyl or ethyl on the nitrogen atom carrying the positive charge, while counterions here are for example chloride, bromide, methosulfate or sulfate.

Contemplated laundry aftertreatments are in particular fabric softeners for application in the final rinse and in the course of fabric care.

Other customary ingredients for such a laundry pre- and aftertreatment are nonionic surfactants, fragrances, dyes, stabilizers, fiber and color protection additives, viscosity modifiers, soil release additives, corrosion inhibitors, bactericides, preservatives and water in the customary amounts.

The novel mixture of components (A) and (B) is highly useful on textile material not only for protecting human skin against harmful UV radiation but also for protecting dyed textile material against fading. Textile material comprising such a mixture of the invention thus likewise forms part of the subject-matter of the present invention.

The inventive mixture of components (A) and (B) provides in particular higher UV protection factors (UPFs). The mixture of the invention further possesses enhanced lightfastness owing to the reduced photodegradation. Moreover, aqueous formulations, preparations and systems comprising the mixture of the invention are more stable oil-in-water emulsions with regard to the hydrophobic UV absorbers, which is attributable to a better particle size distribution of the hydrophobic UV absorber system in the aqueous phase.

The examples hereinbelow are intended to more particularly describe the invention without, however, limiting it.

EXAMPLE 1

Application in Laundry Aftertreatment in Final Rinse Bath and Determination of the UV Protection Factor UPF White woven cotton fabric having a basis weight of 100 $g/mm^2$ [sic] and a UV protection factor UPF of 4.50 was washed using a water hardness of 3 mmol/l. The laundering process was a main wash cycle at 40° C. with a commercially available laundry detergent (Ariel® Color) and a subsequent conditioning rinse. The conditioner used was a commercially available formulation (Lenor® care) in a dosage of 1000 ppm, based on the liquor. The fabric conditioner formulation included either no UV absorber possessing affinity for textile fiber or in each case 50, 100 or 200 ppm, based on the liquor, of an inventive UV absorber mixture M1, M2, M3 or M4 added before the conditioning rinse. After the conditioning rinse cycle, the fabric was removed and its UV protection factor UPF was determined in the dried state.

UV absorber mixtures M1 to M4 used:

M1=75% by weight of 2-ethylhexyl 2-cyano-3,3-diphenylacrylate (Uvinul® N-539 T)+25% by weight of n-hexyl 2-(41-diethylamino-2'-hydroxybenzoyl)benzoate M2=80% by weight of 2-ethylhexyl 2-cyano-3,3-diphenylacrylate+20% by weight of 1-(4-tert-butylphenyl)-3-(4-methoxyphenyl)propane-1,3-dione (Uvinul® BMBM)

M3=75% by weight of 2-ethylhexyl 2-cyano-3,3-diphenylacrylate+25% by weight of 2-hydroxy-4-(2-ethylhexyloxy)benzophenone (Uvinul® 408)

M4=90% by weight of 2-ethylhexyl 2-cyano-3,3-diphenylacrylate+10% by weight of 1,1-bis(neopentyloxycarbonyl)-4,4-diphenyl-1,3-butadiene A1=100% by weight of 2-ethylhexyl 2-cyano-3,3-diphenylacrylate (for comparison)

Table 1 shows the results of the tests:

TABLE 1

|  | UPF with 50 ppm | UPF with 100 ppm | UPF with 200 ppm |
| --- | --- | --- | --- |
| Mixture M1 | 10.5 | 15.4 | 24.0 |
| Mixture M2 | 11.1 | 18.2 | 30.9 |
| Mixture M3 | 9.6 | 16.4 | 28.2 |
| Mixture M4 | 11.2 | 16.7 | 30.1 |
| UV absorber A1 | 8.6 | 13.5 | 21.1 |

UPF without UV absorber: 4.7

The results show that the use of the inventive UV absorber mixtures M1, M2, M3 or M4 leads to higher UV protection factors (UPFs) of the cotton fabric than the sole use of A1 in the same amount.

EXAMPLE 2

Application in Laundry Aftertreatment in Conditioning Rinse and Determination of Photostability of Dyed Cotton Fabric Used Woven cotton fabric dyed with Reactive Black 5 to ⅓ standard depth of shade was treated in the conditioning rinse cycle with a commercially available formulation (Lenor® care, 1000 ppm based on the liquor) in the presence of an inventive UV absorber mixture M1, M2, M3, M4, M5, M6 or M7 (each at 200 ppm based on the liquor) in a liquor ratio of 12.5:1. After the conditioning rinse cycle, the dyed fabric was removed and tested for photostability in the dried state.

UV absorber mixtures M1 to M7 used:

M1 to M4: see Example 1

M5=90% by weight of 2-ethylhexyl 2-cyano-3,3-diphenylacrylate (Uvinul® N-539 T)+10% by weight of 2-(2'-hydroxy-3',5'-di-tert-amylphenyl)-2H-benzotriazole (Tinuvin 328)

M6 =30% by weight of 2-ethylhexyl 2-cyano-3,3-diphenylacrylate+70% by weight of 2-hydroxy-4-(2-ethylhexyloxy)benzophenone M7=50% by weight of 2-ethylhexyl 2-cyano-3,3-diphenylacrylate+50% by weight of mixture of polyoxyethylene glycol β-[3-(2H-benzotriazol-2-yl)-5-tert-butyl-4-hydroxyphenyl]propionate and polyoxyethylene glycol-bis-β-[3-(2H-benzotriazol-2-yl)-5-tert-butyl-4-hydroxy-phenyl]propionate having an average molecular weight of >600 (Tinuvin® 1130)

A1=100% by weight of 2-ethylhexyl 2-cyano-3,3-diphenylacrylate (for comparison)

Photostability was measured as follows:

The samples were exposed in a SUNTEST® tabletop accelerated lighting unit (from Heraeus, Hanau) for 14 hours under outdoor conditions. A spectrophotometer incl. an integration sphere ("Lambda 900" from Perkin Elmer) was used to measure the reflectance spectra of dyeings before and after exposure. These reflectance spectra were converted in line with the Kubelka-Munk theory into K/S spectra (K=absorption coefficient, S=scattering coefficient). The photostabilities are evaluated with reference to the K/S values after 14 hour exposure relative to the K/S values prior to exposure (K/S in each case at the maximum of the K/S spectra). The higher the value in % reported in Table 2, the higher the photostability.

Table 2 shows the results of the measurements:

TABLE 2

| UV absorber | Dosage [ppm] | K/S (14 h)/K/S (0 h) × 100% |
| --- | --- | --- |
| without | — | 65.2% |
| A1 | 200 | 67.7% |
| M1 | 200 | 69.7% |
| M2 | 200 | 70.8% |
| M3 | 200 | 73.3% |
| M4 | 200 | 71.6% |
| M5 | 200 | 72.9% |
| M6 | 200 | 76.5% |
| M7 | 200 | 70.1% |

The results show that the use of the inventive UV absorber mixtures M1 to M7 protects the dyed fabric more effectively against fading due to UV rays than the sole use of UV absorber A1 in the same amount.

EXAMPLE 3

Preparation of Homogeneous Liquid Mixtures of (A) and (B)

The combinations hereinbelow of compounds (A) and (B) formed a common homogeneous and clear liquid phase on being mixed together at room temperature in the absence of solvents or diluents [exemplary weight mixing ratios of (A) to (B) are reported in the brackets]. This enumeration is just an exemplary selection in the context of the present invention of possible mixtures of (A) and (B) which form such homogeneous liquid phases.

Compound (A) was in all cases the 2-ethylhexyl ester of 2-cyano-3,3-diphenylacrylic acid (Uvinul® N-539 T).

The following compounds were used as compound (B):

2-(2'-hydroxy-3',5'-di-tert-amylphenyl)-2H-benzotriazole (Tinuvin® 328) [90:10], 2-(2H-benzotriazol-2-yl)-4-n-octylphenyl (Tinuvin® 329) [90:10], 2-hydroxy-3-sec-butyl-5-tert-butylbenzotriazole (Tinuvin® 350) [80:20], mixture of polyoxyethylene glycol β-[3-(2H-benzotriazol-2-yl)-5-tert-butyl-4-hydroxyphenyl]propionate and polyoxyethylene glycol bis-β-[3-(2H-benzotriazol-2-yl)-5-tert-butyl-4-hydroxyphenyl]propionate having an average molecular weight >600 (Tinuvin® 1130) [50:50, 20:80], 2-hydroxy-3-dodecyl-5-methylphenylbenzotriazole (Tinuvin® 571) [70:30], 2-hydroxy-4-methoxybenzophenone (Uvinul® M40) [80:20], 1-(4-tert-butylphenyl)-3-(4-methoxyphenyl)propane-1,3-dione (Uvinul® BMBM) [80:20], 2-hydroxy-4-(n-octyloxy)benzophenone (Uvinul® 3008) [75:25], 1,1-bis(neopentyloxycarbonyl)-4,4-diphenyl-1,3-butadiene [90:10], n-hexyl 2-(4'-diethylamino-2'-hydroxybenzoyl)benzoate [67:33, 80:20], 2-hydroxy-4-(2-ethylhexyloxy)benzophenone [30:70, 75:25], 1,1-dicyano-2-(4-butyloxy)phenyl-2-phenylethene [90:10], 1,1-bis(neopentyloxycarbonyl)-4,4-diphenyl-1,3-butadiene+2-hydroxy-4-(2-ethylhexyloxy)benzophenone [70:10:20], n-hexyl 2-(4'-diethylamino-2'-hydroxybenzoyl)benzoate+2-hydroxy-4-(2-ethylhexyloxy)benzophenone [40:10:50], mixture of polyoxyethylene glycol β-[3-(2H-benzotriazol-2-yl)-5-tert-butyl-4-hydroxyphenyl] propionate and polyoxyethylene glycol bis-β-[3-(2H-benzotriazol-2-yl)-5-tert-butyl-4-hydroxyphenyl]propionate having an average molecular weight >600 (Tinuvin® 1130)+2-hydroxy-4-(n-octyloxy)benzophenone (Uvinul® 3008) [45:40:15].

We claim:

1. A composition comprising
   (A) from 20 to 80% by weight of at least one $C_6$- to $C_{18}$-alkyl ester or $C_5$- to $C_8$-cycloalkyl ester of 2-cyano-3-diphenylacrylic acid and
   (B) from 80 to 20% by weight of at least one compound which has at least one UV absorption maximum in the range from 280 nm to 450 nm selected from the group consisting of phenylbenzotriazoles, esters of p-aminobenzoic acid, esters of cinnamic acid, esters of salicylic acid, acrylates that are different from said compounds (A), diarylbutadienes and amino-substituted hydroxybenzophenones.

2. A method, comprising:
applying the composition as claimed in claim 1 to a textile material.

3. The method as claimed in claim 2, wherein the applying occurs during textile finishing, laundering, laundry pretreatment, laundry after-treatment or a combination thereof.

4. The method as claimed in claim 2, wherein the textile material is a cellulosic textile material.

5. The method as claimed in claim 2, wherein the composition comprises:
from 30 to 70% by weight of at least one compound (A) and
from 70 to 30% by weight of at least one compound (B).

6. The method as claimed in claim 2, wherein compound (B) has at least one UV absorption maximum in the range from 330 nm to 380 nm.

7. The method as claimed in claim 2, wherein compound (B) has at least one UV absorption maximum in the range from 280 nm to 315 nm with an $E^1_1$ value of at least 200 and at least one UV absorption maximum in the range from 315 nm to 400 nm with an $E^1_1$ value of at least 200.

8. The method as claimed in claim 2, wherein compound (A) and compound (B) are capable of forming a homogeneous liquid phase in a temperature range of from 10° C. to 35° C. without the addition of a solvent or a diluent.

9. The method as claimed in claim 2, wherein compound (B) has an n-octanol/water partition coefficient log P of at least 1.9.

10. The method as claimed in claim 2, wherein compound (B) is selected from the group consisting of
(a) phenylbenzotriazoles,
(b) dibenzoylmethanes,
(c) esters of p-aminobenzoic acid,
(d) esters of cinnamic acid,
(e) esters of salicylic acid,
(f) nitrogen-free 2-hydroxybenzophenones,
(g) phenylbenzimidazoles,
(h) acrylates that are different from said compounds (A),
(i) diarylbutadienes,
(j) amino-substituted hydroxybenzophenones
(k) triazines, and combinations thereof.

11. A textile material obtained by the process as claimed in claim 2.

12. A method comprising
covering human skin with a textile material, wherein said textile material is obtained by applying to the textile material with the composition as claimed in claim 1.

13. The method as claimed in claim 12 wherein the applying occurs during textile finishing, laundering, laundry pretreatment, laundry after-treatment or a combination thereof.

14. The method as claimed in claim 12, wherein the textile material is a cellulosic textile material.

15. The method as claimed in claim 12, wherein the composition comprises
from 30 to 70% by weight of at least one compound (A) and
from 70 to 30% by weight of at least one compound (B).

16. The method as claimed in claim 12, wherein compound (B) has at least one UV absorption maximum in the range from 330 nm to 380 nm.

17. The method as claimed in claim 12, wherein compound (B) has at least one UV absorption maximum in the range from 280 nm to 315 nm with an $E^1_1$ value of at least 200 and at least one UV absorption maximum in the range from 315 nm to 400 nm with an $E^1_1$ value of at least 200.

18. The method of claim 12, wherein compound (A) and compound (B) are capable of forming a homogeneous liquid phase in a temperature range of from 10° C. to 35° C. without the addition of a solvent or a diluent.

19. The method as claimed in claim 12, wherein compound (B) has an n-octanol/water partition coefficient log P of at least 1.9.

20. The method as claimed in claim 12, wherein compound (B) is selected from the group consisting of
(a) phenylbenzotriazoles,
(b) dibenzoylmethanes,
(c) esters of p-aminobenzoic acid,
(d) esters of cinnamic acid,
(e) esters of salicylic acid,
(f) nitrogen-free 2-hydroxybenzophenones,
(g) phenylbenzimidazoles,
(h) acrylates that are different from said compounds (A),
(i) diarylbutadienes,
(j) amino-substituted hydroxybenzophenones
(k) triazines, and combinations thereof.

21. The method as claimed in claim 12, wherein the composition comprises a UV absorber selected from the group consisting of diarylbutadienes, amino-substituted hydroxybenzophenones, and combinations thereof.

22. A laundry detergent comprising from 0.01 to 40wt% by weight of the composition of claim 1.

23. The laundry detergent as claimed in claim 22, wherein the detergent comprises from 0.01 to 20wt.% of the composition.

24. The laundry detergent claimed in claim 22, further comprising from 1 to 50% by weight of one or more cationic surfactants selected from the group consisting of diesterammonium salts, quaternary tetraalkylammonium salts, quaternary diamidoammonium salts, amidoamino esters, imidazolines, and combinations thereof.

25. The composition as claimed in claim 1, wherein the composition comprises
from 30 to 70% by weight of at least one compound (A) and
from 70 to 30% by weight of at least one compound (B).

26. The composition as claimed in claim 1, wherein the composition comprises
from 40 to 60% by weight of at least one compound (A) and
from 60 to 40% by weight of at least one compound (B).

* * * * *